US012662510B2

(12) United States Patent
Manica et al.

(10) Patent No.: US 12,662,510 B2
(45) Date of Patent: Jun. 23, 2026

(54) PROTEIN-TARGETED DRUG COMPOUND IDENTIFICATION

(71) Applicant: INTERNATIONAL BUSINESS MACHINES CORPORATION, Armonk, NY (US)

(72) Inventors: Matteo Manica, Zurich (CH); Maria Rodriguez Martinez, Thalwil (CH); Jannis Born, Zurich (CH); Joris Cadow, Winterthur (CH)

(73) Assignee: International Business Machines Corporation, Armonk, NY (US)

( * ) Notice: Subject to any disclaimer, the term of this patent is extended or adjusted under 35 U.S.C. 154(b) by 1142 days.

(21) Appl. No.: 17/004,104

(22) Filed: Aug. 27, 2020

(65) Prior Publication Data

US 2020/0392178 A1    Dec. 17, 2020

Related U.S. Application Data

(63) Continuation-in-part of application No. 16/685,455, filed on Nov. 15, 2019, now Pat. No. 11,651,841, which is a continuation-in-part of application No. 16/413,399, filed on May 15, 2019, now Pat. No. 11,651,860.

(51) Int. Cl.
| | |
|---|---|
| *C07K 1/04* | (2006.01) |
| *G16B 5/00* | (2019.01) |
| *G16C 20/50* | (2019.01) |

(52) U.S. Cl.
CPC ................ *C07K 1/047* (2013.01); *G16B 5/00* (2019.02); *G16C 20/50* (2019.02)

(58) Field of Classification Search
CPC ........... C07K 1/047; G16B 5/00; G16C 20/50
See application file for complete search history.

(56) References Cited

U.S. PATENT DOCUMENTS

| | | | |
|---|---|---|---|
| 11,651,841 B2 | 5/2023 | Oskooei et al. | |
| 11,651,860 B2 | 5/2023 | Oskooei et al. | |
| 2014/0057798 A1 | 2/2014 | Gong et al. | |
| 2017/0193157 A1 | 7/2017 | Quirk et al. | |
| 2021/0264110 A1* | 8/2021 | McCarthy | ............. G16C 20/50 |

FOREIGN PATENT DOCUMENTS

| | | |
|---|---|---|
| CN | 107609326 A | 1/2018 |
| WO | WO2019018780 A1 | 1/2019 |

OTHER PUBLICATIONS

Petrova, Innovation in the pharmaceutical industry: The process of drug discovery and development, in Innovation and marketing in the pharmaceutical industry, Springer, 2014, pp. 19-81.

Goh et al., SMILES2Vec: An Interpretable General-Purpose Deep Neural Network for Predicting Chemical Properties, ArXiv Prepr. ArXiv171202034, 2017, 8 Pages.

Chang, et al., Cancer Drug Response profile scan (CDRscan): a deep learning model that predicts drug effectiveness from cancer genomic signature, Scientific reports. Jun. 11, 2018;8(1):8857.

Oskooei et al., PaccMann: Prediction of anticancer compound sensitivity with multi-modal attention-based neural networks, arXiv:1811.06802v1 [cs.LG], Nov. 16, 2018. Grace Period Disclosure pp. 1-13.

Bahdanau et al., Neural machine translation by jointly learning to align and translate, arXiv preprint arXiv:1409.0473, 2014, 15 pages.

Vaswani et al., Attention is all you need, Advances in neural information processing systems, 2017, pp. 5998-6008.

Yang et al., Hierarchical attention networks for document classification, Proceedings of the 2016 conference of the North American chapter of the association for computational linguistics: human language technologies, Jun. 2016, pp. 1480-1489.

Schwaller, et al., Found in Translation: predicting outcomes of complex organic chemistry reactions using neural sequence-to-sequence models, Chemical science, 9(28), 2018, pp. 6091-6098. DOI: 10.1039/C8SC02339E.

Lloyd, et al., Pharma r&d annual review 2017, Available at: pharmaintelligence.informa.com/resources/product-content/pharma-rd-annual review-2018, Accessed Jun. 25, 2018, 2017, 44 pages.

Hargrave-Thomas, et al., Serendipity in anticancer drug discovery, World journal of clinical oncology 3.1, 2012, 17 pages doi: 10.5306/wjco.v3.i1.1.

Garnett, et al., Systematic identification of genomic markers of drug sensitivity in cancer cells, Nature 483 No. 7391. 2012, pp. 570-575 (Abstract Only).

(Continued)

*Primary Examiner* — Jerry Lin
(74) *Attorney, Agent, or Firm* — CHIP LAW GROUP

(57)    ABSTRACT

Methods and systems are provided for identifying drug compounds for targeting proteins in tissue cells. Such a method includes providing a neural network model which comprises an attention-based protein encoder and a molecular decoder. The protein encoder is pretrained in an autoencoder architecture to encode an input protein sequence into an output vector in a latent space representing proteins. The molecular decoder is pretrained in an autoencoder architecture to generate compound data, defining a compound molecule, from an input vector in a latent space representing molecules. The protein encoder and molecular decoder are coupled such that the input vector of the molecular decoder is dependent on the output vector of the protein encoder for an input protein sequence.

21 Claims, 5 Drawing Sheets

(56) References Cited

OTHER PUBLICATIONS

Yang et al., Genomics of Drug Sensitivity in Cancer (GDSC): a resource for therapeutic biomarker discovery in cancer cells, Nucleic acids research 41.D1, 2012, pp. D955-D961.

Barretina et al., The Cancer Cell Line Encyclopedia enables predictive modeling of anticancer drug sensitivity, Nature 483, No. 7391, 2012, pp. 603-607 (Author Manuscript).

Cancer Genome Atlas Network. Comprehensive molecular portraits of human breast tumours, Nature 490, No. 7418 (2012): 61-70.

Heiser, et al., Subtype and pathway specific responses to anticancer compounds in breast cancer, Proceedings of the National Academy of Sciences, 2012, 109(8), pp. 2724-2729.

International Cancer Genome Consortium, International network of cancer genome projects, Nature 464, 7291, 2010, pp. 993-996.

Lamb, et al., The Connectivity Map: using gene-expression signatures to connect small molecules, genes, and disease, Science, 313(5795), 2006, pp. 1929-1935.

Shoemaker, The NCI60 human tumor cell line anticancer drug screen, Nature Reviews Cancer 6, No. 10, 2006, pp. 813-823.

Costello, et al., A community effort to assess and improve drug sensitivity prediction algorithms, Nature biotechnology 32, No. 12, 2014, pp. 1202-1214.

Geeleher, Cancer biomarker discovery is improved by accounting for variability in general levels of drug sensitivity in pre-clinical models, Genome biology 17, No. 1, 2016, 190, 11 pages.

Menden et al., Machine learning prediction of cancer cell sensitivity to drugs based on genomic and chemical properties, PLOS one vol. 8, No. 4, 2013, e61318, 10 pages.

Karelson, et al., Quantum-chemical descriptors in QSAR/QSPR studies, Chem. Rev., vol. 96, No. 3, pp. 1027-1044, 1996.

Cereto-Massague, et al., Molecular fingerprint similarity search in virtual screening, Methods 71, 2015, pp. 58-63.

Luong et al., Effective approaches to attention-based neural machine translation, arXiv preprint arXiv:1508.04025, 2015, 11 pages.

Wu et al., Google's neural machine translation system: Bridging the gap between human and machine translation, arXiv preprint arXiv:1609.08144, 2016, 23 pages.

Chen et al., The rise of deep learning in drug discovery, Drug Discovery Today, vol. 23, No. 6, pp. 1241-1250, Jun. 2018.

Chang et al., Cancer Drug Response profile scan (CDRscan): a deep learning model that predicts drug effectiveness from cancer genomic signature, Scientific reports 8, No. 1, 2018, 11 pages.

Oskooei et al., PaccMann: Prediction of anticancer compound sensitivity with multi-modal attention-based neural networks, arXiv preprint arXiv:1811.06802, 2018, 13 pages.

Manica et al., Towards Explainable Anticancer Compound Sensitivity Prediction via Multimodal Attention-based Convolutional Encoders, ICML2019, Jun. 14, 2019, Grace Period Disclosure 11 Pages.

Manica et al., Deep learning for disease-driven drug design, https://www.meetup.com/Deep-Learning-Zurich-DLZH/events/261927228/, Jun. 25, 2019. Grace Period Disclosure 51 Pages.

Merolla et al., A Million Spiking-Neuron Integrated Circuit with a Scalable Communication Network and Interface, Science, vol. 345, Issue 6197, 2014, 7 pages.

Yang et al., Hierarchical Attention Networks for Document Classification, Proceedings of the 2016 Conference of the North American Chapter of the Association for Computational Linguistics: Human Language Technologies, pp. 1480 to 1489, 2016.

Willia, Simple Statistical Gradient-Following Algorithms for Connectionist Reinforcement Learning, Mach. Learn. 8, 229-256 (1992).

Le Tourneau et al., Treatment Algorithms Based on Tumor Molecular Profiling: The Essence of Precision Medicine Trials, JNCI Journal of the National Cancer Institute, 2016, 108(4): djv362, 10 pages.

Olivecrona et al., Molecular De-Novo Design through Deep Reinforcement Learning, Cornell University Library, Computer Science, Artificial Intelligent, arXiv:1704.07555, Apr. 25, 2017.

Seyed Ali Kazemi Oskooei et al., unpublished U.S. Appl. No. 16/413,399, filed May 15, 2019, Drug Efficacy Prediction for Treatment of Genetic Disease, pp. 1-25 plus 5 sheets of drawings.

Alan Harrison, List of IBM Patents or Patent Applications Treated as Related, Nov. 27, 2022, pp. 1-2.

* cited by examiner

PIK3CA

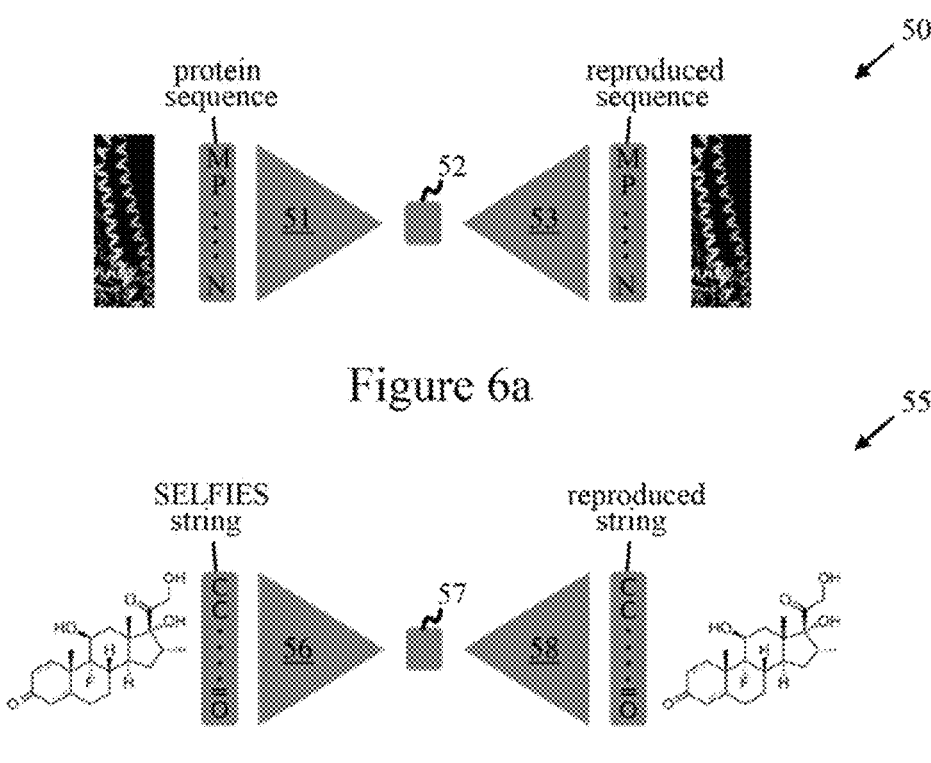
Figure 6a
Figure 6b
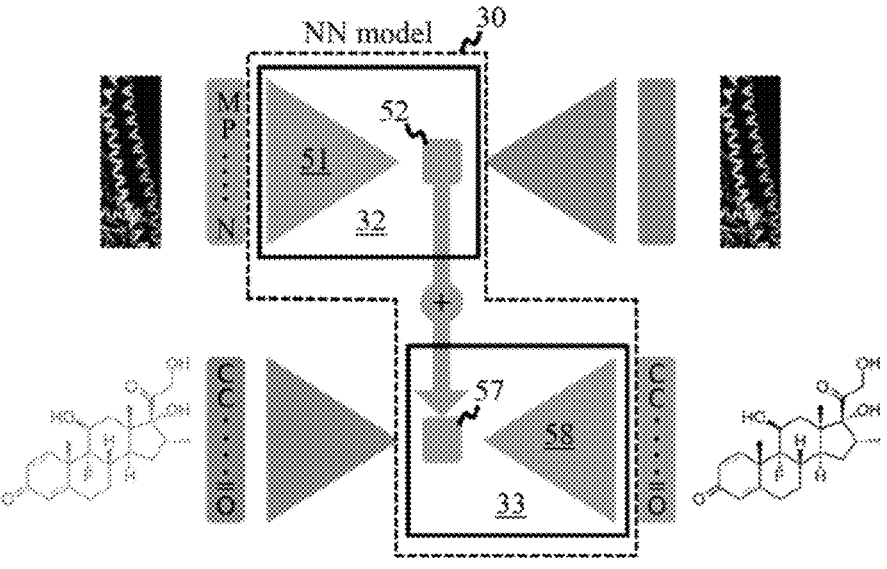
Figure 7

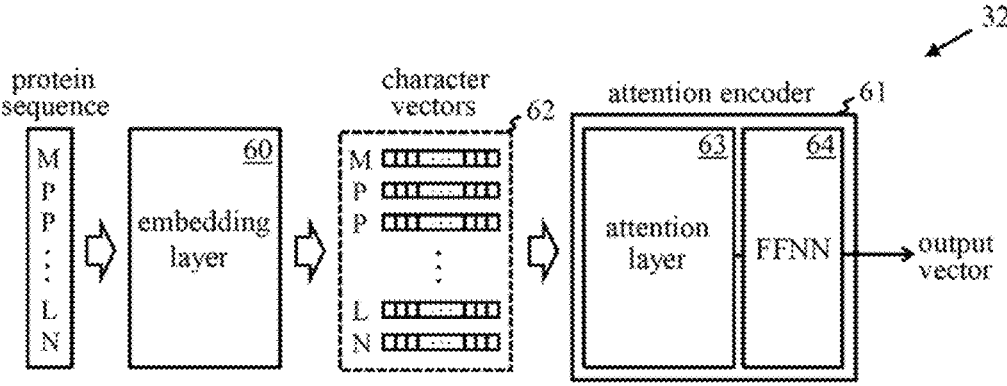
Figure 8
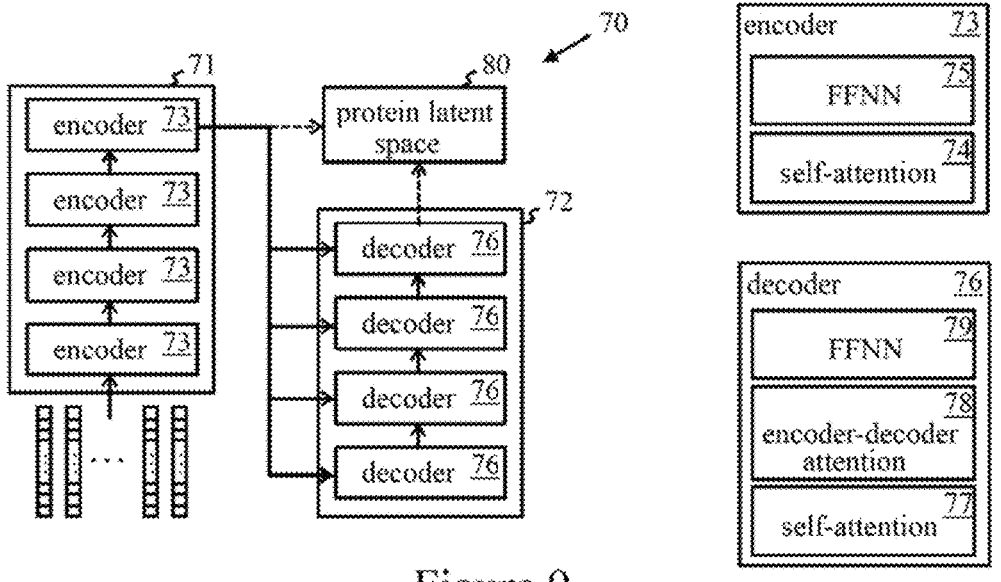
Figure 9
Figure 10

PROTEIN-TARGETED DRUG COMPOUND IDENTIFICATION

STATEMENT REGARDING PRIOR DISCLOSURES BY THE INVENTOR OR A JOINT INVENTOR

The following disclosures are submitted under 35 U.S.C. 102(b)(1)(A): "Reinforcement learning-driven de-novo design of anticancer compounds conditioned on biomolecular profiles", Jannis Born, Matteo Manica, Ali Oskooei, Maria Rodriguez Martinez, arXiv:1909.05114v1 [q-bio.BM], 29 Aug. 2019, "PaccMann$^{RL}$: Designing anticancer drugs from transcriptomic data via reinforcement learning", Jannis Born, Matteo Manica, Ali Oskooei, Joris Cadow, Karsten Borgwardt, Maria Rodriguez Martinez, arXiv:1909.05114v4 [q-bio.BM], 16 Apr. 2020; and "PaccMann$^{RL}$ on SARS-CoV-2: Designing antiviral candidates with conditional generative models", Jannis Born, Matteo Manica, Joris Cadow, Greta Markert, Nil Adell Mill, Modestas Filipavicius, Maria Rodriguez Martinez, arXiv: 2005.13285v2 [q-bio.QM], 31 May 2020.

BACKGROUND

The present invention relates generally to protein-targeted drug compound identification. Methods are provided for identifying drug compounds for targeting proteins in tissue cells based on protein sequences for the target proteins. Apparatus and computer program products implementing such methods are also provided.

SUMMARY

One aspect of the present invention provides a method for identifying drug compounds for targeting proteins in tissue cells. The method includes providing a neural network model which comprises an attention-based protein encoder and a molecular decoder. The protein encoder is pretrained in an autoencoder architecture to encode an input protein sequence into an output vector in a latent space representing proteins. The molecular decoder is pretrained in an autoencoder architecture to generate compound data, defining a compound molecule, from an input vector in a latent space representing molecules. The protein encoder and molecular decoder are coupled such that the input vector of the molecular decoder is dependent on the output vector of the protein encoder for an input protein sequence. The method includes training the model in a reinforcement learning architecture in which reward values dependent on affinity of compound molecules, which are defined by compound data generated by the molecular decoder for respective protein sequences encoded by the protein encoder, to proteins corresponding to those sequences are used to progressively train the model to optimize the reward value for compound data generated thereby. The method further comprises, after training the model, supplying a protein sequence for a target protein to the model to generate compound data corresponding to a set of drug compounds for targeting that protein.

Respective further aspects of the invention provide a system for implementing methods for identifying drug compounds as described above, and a computer program product comprising a computer readable storage medium embodying program instructions, executable by a computing system, to cause the computing system to perform such methods.

Embodiments of the invention will be described in more detail below, by way of illustrative and non-limiting example, with reference to the accompanying drawings.

BRIEF DESCRIPTION OF THE DRAWINGS

FIGS. 6a and 6b illustrate architectures for pretraining components of a neural network model of the FIG. 5 system;

FIG. 7 illustrates architecture of the pretrained neural network model;

FIG. 8 is a schematic representation of an attention-based protein encoder of the neural network model;

FIG. 9 shows an alternative structure for the attention-based protein encoder;

FIG. 10 is a schematic representation of a critic neural network in the FIG. 5 system;

DETAILED DESCRIPTION

Figure 1:
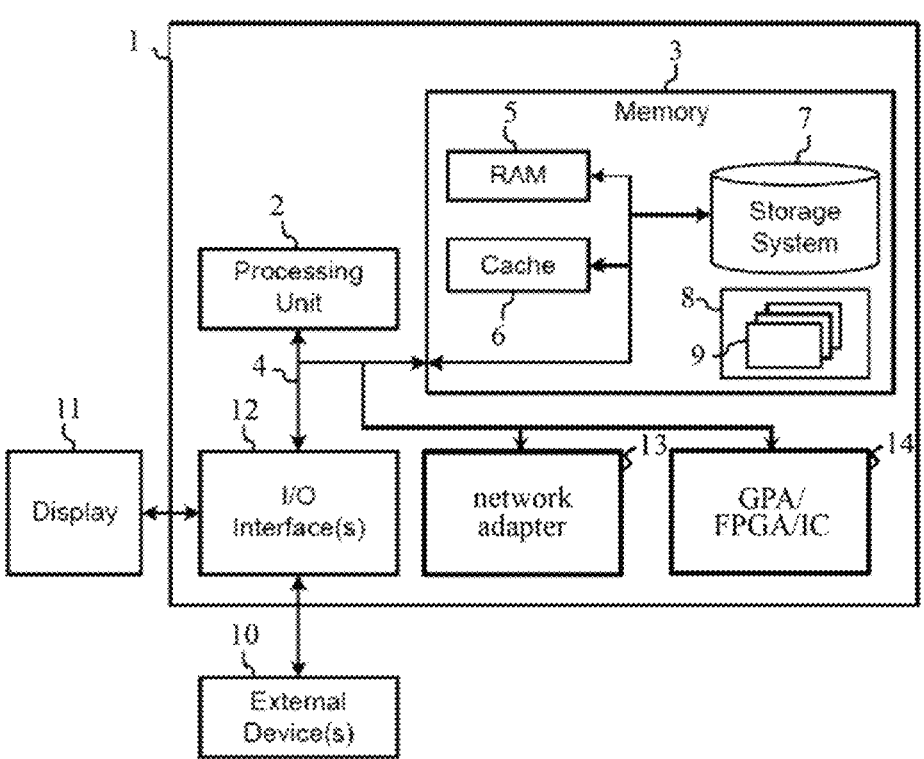
FIG. 1 is a schematic representation of a computing system for implementing methods embodying the invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Protein-targeted drug identification methods embodying the invention may be performed as computer-implemented methods in which neural network models are implemented by software in a computing system. Other embodiments of the invention may employ neural network models implemented (wholly or partially) in hardware. Methods embodying the invention may be implemented (wholly or partially) by a computing system comprising one or more general- or special-purpose computers, each of which may comprise one or more (real or virtual) machines, providing functionality for implementing operations described herein. Steps of methods embodying the invention may be implemented by program instructions, e.g. program modules, implemented by a processing apparatus of the system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

FIG. 1 is a block diagram of exemplary computing apparatus for implementing methods embodying the invention. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA)

bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

Memory 3 may include at least one program product having one or more program modules that are configured to carry out functions of embodiments of the invention. By way of example, program/utility 8, having a set (at least one) of program modules 9, may be stored in memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g., network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g., the Internet) via network adapter 13. As depicted, network adapter 13 communicates with the other components of computer 1 via bus 4. Computer 1 may also communicate with additional processing apparatus 14, such as one or more GPUs (graphics processing units), FPGAs, or integrated circuits (ICs), for implementing embodiments of the invention. It should be understood that although not shown, other hardware and/or software components could be used in conjunction with computer 1. Examples include, but are not limited to: microcode, device drivers, redundant processing units, external disk drive arrays, RAID systems, tape drives, and data archival storage systems, etc.

Embodiments described below exploit machine learning models based on neural networks. Neural network models perform computational tasks in a manner inspired by biological architectures of the nervous system. These models are based on a fundamental principle of biological systems whereby neurons are interconnected via synapses which relay weighted signals between the neurons. Neural network architectures exploit a logical construction in which a series of layers of neurons are interconnected so that output signals of neurons in one layer are weighted and transmitted to neurons in the next layer. Each neuron in a given layer can be connected to one or more neurons in another layer, and different weights can be associated with respective neuron-neuron connections. Each neuron generates output signals dependent on its accumulated inputs, whereby weighted signals can be propagated over layers of the network. The sets of weights associated with the various layers of a neural network are learned during a model training operation. The weights are trained via an iterative process in which the network is exposed to a set of training data and the weights are repeatedly updated as the network "learns" from the training data. Training involves an iterative cycle of signal propagation and weight-update operations, with the network weights being progressively updated until a convergence condition is achieved. The resulting trained network model, with the trained (optimized) weights defined via this process, can then be applied for inference to new (previously unseen) input data.

Figure 2:
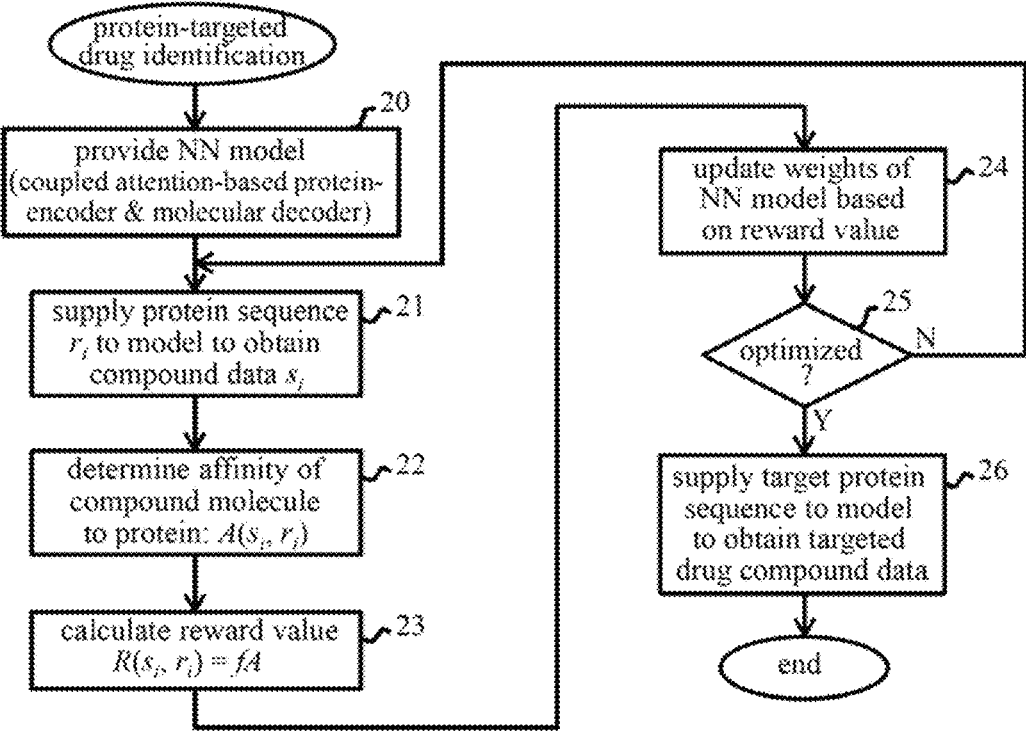
FIG. 2 indicates steps of a protein-targeted drug identification method embodying the invention.
Figure 3:
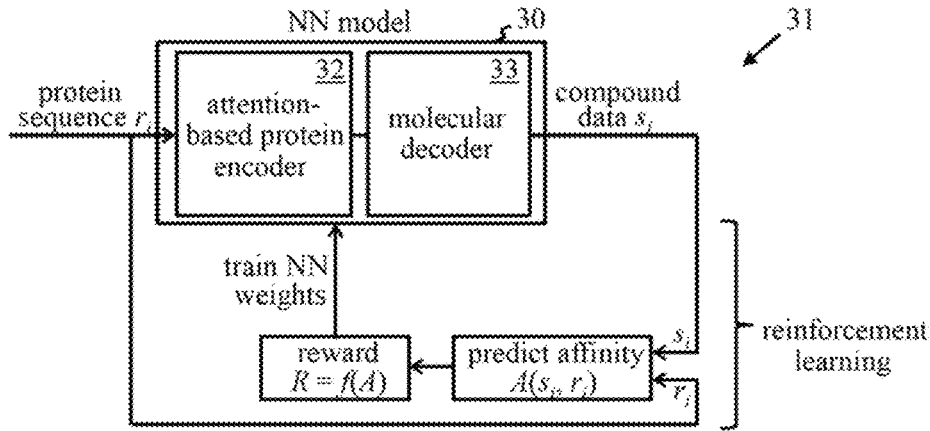
FIG. 3 is a schematic representation of a neural network model in a reinforcement learning architecture employed in the FIG. 2 method.

FIG. 2 indicates basic steps of a method embodying the invention for identifying drug compounds for targeting proteins in tissue cells. The method employs a neural network (NN) model which is implemented in step 20 of FIG. 2. The basic structure of this model is illustrated in FIG. 3 where the model 30 is shown connected in a reinforcement learning architecture 31. The model 30 comprises an attention-based protein encoder 32 and a molecular decoder 33. As explained in more detail below, the protein encoder 32 is pretrained in an autoencoder architecture to encode an input protein sequence into an output vector in a latent space representing proteins. The molecular decoder 33 is pretrained in an autoencoder architecture to generate compound data, defining a compound molecule, from an input vector in a latent space representing molecules. The protein encoder and molecular decoder are coupled in model 30 such that the input vector of the molecular decoder is dependent on the output vector of the protein encoder for an input protein sequence. The resulting compound data generated by molecular decoder 33 is thus conditioned on the protein sequence input to protein encoder 32.

The NN model 30 is trained using a reinforcement learning (RL) architecture 31 via an iterative training process indicated in steps 21 to 25 of FIG. 2. In step 21 of each iteration i of this process, computing system 1 supplies a protein sequence $r_i$ to the model to obtain compound data $s_i$ for a compound molecule. In step 22, system 1 determines the affinity of the compound molecule defined by the output compound data $s_i$ to the protein corresponding to the input protein sequence r Affinity, denoted here by $A(s_i, r_i)$, may be variously defined, e.g. in terms of binding affinity of the molecule to the protein, protein selectivity of the molecule, or a combination of these and/or similar affinity metrics. The affinity $A(s_i, r_i)$ may be estimated or otherwise determined in various ways as discussed below. In step 23, system 1 calculates a reward value $R(s_i, r_i)$ dependent on the affinity $A(s_i, r_i)$ determined in step 22. The reward value R is determined here as a function, denoted by f, of the affinity A. In step 24, system 1 updates the network weights of NN model 30 in dependence on the reward value R so as to progress towards a more optimal state (producing higher reward values, i.e. more optimal compounds). In step 25, system 1 checks whether a convergence condition, indicating optimized weights in model 30, has been achieved. If not ("N" at decision step 25), operation reverts to step 21 for a further iteration of the training operation. Steps 21 to 25 thus implement an iterative training process in which reward values dependent on affinity of compound molecules, defined by compound data generated by the molecular decoder for respective protein sequences encoded by the protein encoder, to proteins corresponding to those sequences are used to progressively train the model to optimize the reward value for compound data generated thereby.

When the weights of model 30 have been optimized ("Y" at decision step 25), the model is fully trained and can be applied for inference without further reinforcement learning. After training the model, system 1 supplies a protein sequence for a target protein (which need not have been seen during training) to the model to generate compound data corresponding to a set of drug compounds for targeting that protein. Compound data may be obtained here for a set of one or more drug compounds, with compound data for a plurality of drugs being obtained by iteratively supplying the target protein sequence to the model, or by otherwise controlling model operation as explained below.

Figure 4:
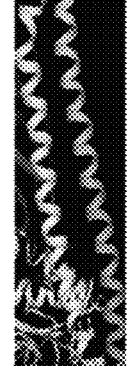
FIG. 4 shows an exemplary protein sequence for a target protein.

The iterative training process trains model 30 as a conditional generative model which can then generate compound data, conditioned on target protein sequences, such that molecules defined by the compound data have high affinity to the target proteins. Proteins are complex biomolecules comprising long chains of amino acids, and different proteins differ mainly in the particular amino acid sequence ("protein sequence") making up each protein. FIG. 4 indicates the protein sequence for an exemplary protein, PIK3CA. The protein sequence is defined as a sequence of letters each representing a particular amino acid. Unlike more detailed protein structure representations, protein sequences are easy to acquire, being readily available from various public sources, and provide a comparatively simple protein representation. The attention-based protein encoder 32 allows these sequences to be ingested and processed by the model in a manner which accommodates the amino acid sequence information. Attention-based encoders are well-known in the machine learning field and are widely applied in language processing applications. Briefly, attention-based encoders project the input into an attention space and distribute attention over different parts of the input, according to different weights which determine the degree of importance attached to the various parts of the input. These attention weights, which are learned during the model training process, are used to comparatively weigh different features of the input according to their relative contribution to a better overall model output. The encoder inputs are filtered using these attention weights, and the filtered feature set is typically further processed by a set of feed-forward network layers to obtain the encoder output.

In the present case, the weights (including attention weights) of protein encoder 32 are trained twice, once in a pretraining operation and again in the RL architecture. Pretraining is performed in a protein environment such that the encoder learns to encode input protein sequences into respective output vectors in a latent space representing proteins, using as objective the reconstruction of the input sequence itself. Here, the encoder learns to encode protein sequences into the latent space, with the attention mechanism ensuring that the encoder can capture the important rules of the protein "grammar" in a similar manner to language understanding techniques. The protein sequence vectors in this latent space thus provide a meaningful protein representation, and the compressed protein structure information is then used, via further training in the RL architecture, to condition the generation of candidate drug compounds for optimal affinity to target proteins. The initial, decoupled pretraining of the protein encoder and molecular encoder is unsupervised, requiring no annotated training data, and produces latent spaces representing protein and compound information respectively. The subsequent RL training allows co-learning of representations between these two drastically different spaces. Given the limited size of the amino acid dictionary, as well as the wide availability of open databases for protein sequence data and affinity data for compounds and proteins, the training process can be extremely efficient.

It will be seen that the above method offers a highly efficient process which leverages language understanding techniques to encode protein sequences and map proteins to compounds based on molecular affinity to protein targets. This provides an elegant and effective technique for de novo design of pharmaceutical drugs to target proteins in tissue cells.

In general, NN model 30 (and additional NN structures described below) may be implemented in hardware or software or a combination thereof. Various implementations for neurons and synapses are known in the art, including circuits which exploit memristive properties of nanodevices, e.g. resistive memory cells such as phase-change memory (PCM) cells. Dense cross-bar arrays of such memristive devices offer massively parallel and highly area- and energy-efficient neural networks. Neural network architectures can be efficiently implemented in integrated circuits (see, for example, "A Million Spiking-Neuron Integrated Circuit with a Scalable Communication Network and Interface", Merolla et al., Science, Vol. 345, Issue 6197, 2014). Memristive devices based on resistive RAM (RRAM, or ReRAM) cells including conductive bridge RRAM cells, oxide or metal-oxide RRAM cells, and carbon RRAM cells may also be employed for neuron/synapse implementation. In general, neurons/synapses can be implemented in any desired manner with particular network functionality provided by hardware and/or software.

Network training can employ a variety of well-known techniques in which weight updates are calculated in order maximize/minimize some predefined function of the reward values. In general, network weights may be updated after every iteration, or after accumulating weight-updates calculated over a set of iterations for a batch of input protein sequences. Convergence (optimization) conditions can be defined in various ways, e.g. as the point at which no further improvement is achieved, or improvement is less than some threshold value, and the particular convergence condition is orthogonal to the operation described herein.

In preferred embodiments below, the compound data defining a compound molecule comprises a string representation of the molecule. String representations (such as SMILES (Simplified Molecular-Input Line-Entry System) strings, SMARTS (SMILES Arbitrary Target Specification) strings, and SELFIES (Self-Referencing Embedded Strings) are well-known line notations for representing the chemical structure of a molecule in a raw form. These raw data strings are distinct from other representations, such as fingerprints or chemical descriptors, which are based on engineered features that describe the chemical properties and structure of a compound. In general, however, compound data may comprise any data representation of a compound molecule, including strings, fingerprints, graphs and chemical descriptors.

Affinity $A(s_i, r_i)$ may be determined in various ways in step 22 of FIG. 2. Embodiments might be envisaged in which system 1 estimates affinity by comparing generated compound data with existing molecules for which affinity data has been published for the target protein. In preferred embodiments, however, affinity is predicted using an additional neural network structure described below. The reward values $R(s_i, r_i)$ may comprise the raw affinity values per se, or another function f thereof, to reward higher affinity values.

Figure 5:
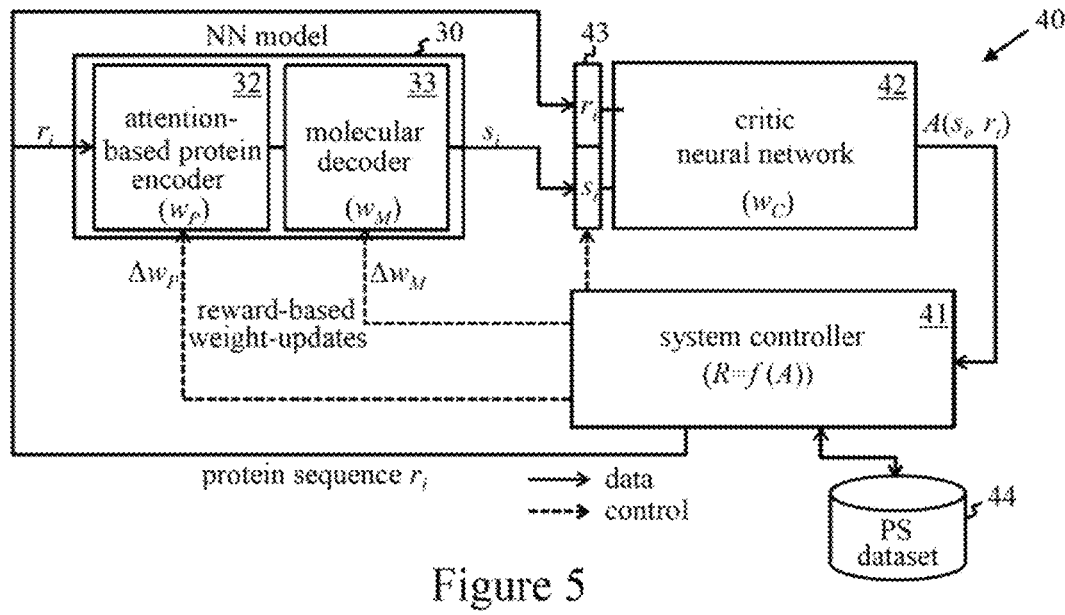
FIG. 5 is a schematic representation of a system embodying the invention for identifying protein-targeted drug compounds.

Exemplary embodiments will now be described in more detail. FIG. 5 shows the RL architecture of a preferred drug identification system embodying the invention. The system 40 includes the NN model 30 described above, where the protein encoder 32 has pretrained weights (which include the attention weights) $w_P$ and the molecular decoder has pretrained weights $w_M$. The system includes control logic comprising a system controller 41 and a critic neural network 42 which generates affinity values in the RL architecture. The critic network 42 comprises a deep neural network, with pretrained weights $w_C$, which receives a data pair, indicated at 43, comprising a protein sequence $r_i$ input to NN model 30 and the compound data $s_i$ output by molecular decoder 33 for that sequence. The critic 42, described further below, is pretrained to output an affinity value $A(s_i, r_i)$ for the input data pair 43. System controller 41 controls overall operation of system 40 in the training and inference processes. Particular controller functionality may be implemented by one or a combination of hardware and software, and suitable implementations will be apparent to those skilled in the art from the operation described herein.

The protein encoder 32 and molecular decoder 33 of model 30 are pretrained in respective autoencoder architectures, in this case variational autoencoders (VAEs), as indicated schematically in FIGS. 6a and 6b. FIG. 6a illustrates the training architecture for protein encoder 32. Autoencoders are well known in the art and need not be described in detail here. Briefly, however, the protein autoencoder 50 of FIG. 6a comprises an encoder network 51 having a series of network layers which encode input protein sequences into parameters of a distribution (e.g. a Gaussian with defined mean and variance) that can be used to sample points in a latent space, indicated at 52, with reduced dimensions compared to the network input. The output of encoder 51 is used to sample a point in latent space 52 that is then supplied as the input to a decoder network 53 which produces an output corresponding to the original input of encoder 51. The protein VAE 50 can be trained from a dataset of protein sequences, e.g. from the UniProt (SwissProt) dataset. Training is performed to optimize weights of encoder 51 and decoder 53 so that the decoder output resembles the encoder input as closely as possible.

FIG. 6b shows a similar autoencoder architecture for molecular strings, implemented here as a VAE for SELFIES strings. The SELFIES strings received by VAE 55 are encoded by an encoder network 56. The encoder output is used to sample a point in latent space 57. This is then supplied to decoder network 58 which attempts to reconstruct the original input string. Training here uses a dataset of strings for bioactive compounds, e.g. the ChEMBL dataset, to optimize the network weights for optimal reconstruction of input strings.

After pretraining, the NN model 30 of system 40 is constructed as shown in FIG. 7 by coupling the encoder network 51 of protein autoencoder 50 and the decoder network 58 of molecular autoencoder 55. An output of protein encoder network 51 is used to sample a point in latent space 52. This is then mapped to a point in latent space 57 of molecular decoder network 58 via a mapping function, in this example by addition of the protein output point in latent space 52 to the origin (zero input) in latent space 57.

FIG. 8 shows a more detailed implementation for encoder network 51 of FIGS. 6b and 7 which forms the attention-based protein encoder 32 of model 30. In this embodiment, the protein encoder 32 comprises an embedding layer 60 and an attention encoder 61.

Embedding layer 60 receives the input protein sequence and encodes characters of the sequence into respective character vectors in a character-embedding space indicated schematically at 62. The characters are typically individual amino acids, represented by single letters, but some predefined amino acid groups (represented by small strings of letters) might be treated as individual characters where these are known to function as a unit. Embedding layer 60 may be implemented, for example, using a standard word embedding scheme where the "words" here correspond to characters of the protein sequence. The resulting matrix of character vectors is supplied to attention encoder 61. This has an attention layer 63 which filters the input vectors according to the pretrained attention weights. The output of attention layer 63 is supplied to a feed-forward neural network (FFNN) 64 which produces the (length-invariant) output vector of the protein encoder.

Use of attention layer 63 in protein encoder 32 ensures that the encoding takes account of the relative positions, or "context", of characters in the protein sequence. In particular, a standard word embedding scheme (as in embedding layer 60) generates the same vector for each instance of the same word (here character) in the input. After attention encoding, however, vectors for different instances of the same character will be modified according to the context of each character instance. Protein encoder 32 thus applies the learnt rules of the protein grammar in producing the final output vector for each sequence. Initial embedding layer 60 improves overall accuracy of the encoding operation compared to attention encoding of the raw protein sequence.

Note that, while a single attention encoder 61 is shown in FIG. 8, in practice multiple "attention heads", each comprising an attention encoder 61 with associated attention weights, may be connected in series to further improve encoder performance.

FIG. 9 shows an alternative protein encoder implementation based on a transformer architecture. Transformers are well known neural network architectures for language processing applications. These models have an encoder/decoder structure in which the encoder applies attention over the model input and the decoder applies attention to both the decoder input and the encoder output. In this embodiment, protein encoder 70 has a multi-head encoder component 71 and corresponding decoder component 72. Each encoder layer 73 of encoder component 71 comprises a self-attention layer 74 and an FFNN 74 as illustrated. Each decoder layer 76 of decoder component 72 comprises a self-attention layer 77 and an encoder-decoder attention layer 78 followed by an FFNN 79. The input to model 70 is again a set of character vectors produced by an embedding stage (not shown) for a protein sequence as described above. Encoder layers 73 sequentially process the input, first with a respective set of attention weights in the self-attention stage 74 and then in FFNN 75. Each layer here may also comprise multiple parallel heads. The output of encoder component 71 in latent space 80 is supplied to each decoder layer 76 of decoder component 72. The decoder layers again process their inputs sequentially. During this process, each decoder layer applies attention over that layer's input in self-attention layer 77, and then combines the result with an attention mechanism over the encoder output in encoder-decoder attention layer 78. The output of decoder component 72 is then combined with the encoder component output in latent space 80 to produce the final output vector for the input protein sequence.

The transformer structure offers enhanced performance and can exploit powerful language processing techniques such as the BERT (Bidirectional Encoder Representations from Transformers), RoBERTa and XLNet techniques which can still be trained very efficiently over the amino acid dictionary. The transformer-based protein encoder 70 may be trained generally as described above, e.g. in an VAE architecture for proteins. In general, however, the protein encoders 32, 70 may be pretrained in any convenient autoencoder architecture, including architectures based on RNNs (Recurrent Neural Networks), CNNs (Convolutional Neural Networks) or GANs (Generative Adversarial Networks), for example.

Molecular decoder 33, which may or may not be attention-based, can be pretrained in any convenient autoencoder architecture and implemented using any generative model for molecules, e.g. based on CNNs, RNNs, GANs, Seq2seq (Sequence-to-Sequence) networks, etc. Note also that the molecular strings may be tokenized in various ways, e.g. by character or by atom, prior to input to these architectures.

FIG. 10 illustrates structure of the critic network 42 in system 40. The critic 42 is a deep neural network which is pretrained to generate, from an input protein sequence $r_i$ and input compound data (here SELFIES string) $s_i$ defining a compound molecule, an affinity value $A(s_i, r_i)$ indicating affinity of the compound molecule to the protein corresponding to sequence $r_i$. Critic 42 comprises a protein-sequence (PS) attention encoder 85 which receives the protein sequence $r_i$ of a data pair 43, and a molecular string attention encoder 86 which receives the compound data $s_i$ of the pair. PS encoder 85 applies an attention mechanism over $r_i$ to produce an encoded protein sequence, and molecular string encoder 86 applies an attention mechanism over $s_i$ to produce an encoded string. The resulting encoded pair (encoded protein sequence plus encoded string) are fed to a final set of dense FF layers 87 which outputs the affinity value $A(s_i, r_i)$. The network weights, including attention weights of encoders 85 and 86, of the critic are learned in a pretraining process which uses a dataset of drug-protein binding affinity. This embodiment used data from the Binding DB (a public database of measured binding affinities between about 7000 proteins and 800,000 small drug-like compounds) in a supervised learning process to train the critic to generate affinity values corresponding (as closely as possible) to those specified in the database for training data pairs.

Referring back to FIG. 5, operation of system 40 involves further training of the weights $w_P$ and $w_M$ of model 30 in the reinforcement learning architecture. System controller 41 extracts protein sequences $r_i$ from a PS dataset 44 and supplies each sequence to NN model 30. Controller 41 also supplies the sequence r together with the resulting string $s_i$ generated by model 30, as a data pair 43 to critic 42. The affinity value $A(s_i, r_i)$ produced by the critic for the data pair is received by controller 41 which calculates a reward value $R=f(A)$ for the molecule generated by model 30. Controller 41 then calculates weight-updates $\Delta w_P$ and $\Delta w_M$ for respective weights $w_P$ and $w_M$ of the model. Weight-updates can be calculated in generally known manner based on a variety of training algorithms. For example, weight updates may be calculated using a REINFORCE algorithm (see, e.g., "Simple Statistical Gradient-Following Algorithms for Connectionist Reinforcement Learning", R. J. Williams, Mach. Learn. 8, 229-256 (1992)) and backpropagation of gradients in model 30 for the reward value for the current iteration.

The training process iterates for successive training examples, with the model weights being progressively updated to improve the reward values for the generated molecules. In this operation, reward values can be calculated in controller 41 using any function which correlates reward with improved affinity.

After training model 30, controller 41 can use the model to generate candidate drug compounds conditioned on any desired target protein. Target proteins may be selected, for example, by comparing protein expression values of disease tissue cells, such as cancer cells from biopsies, with healthy tissue cells to identify targets specific to a disease. For a given target protein, controller 41 preferably controls model 30 to generate a plurality of compound molecules. This may be achieved by iteratively supplying the target protein sequence to the model and relying on inherent stochasticity of the neural network to generate a set of candidate molecules for the target protein. Alternatively, controller 41 may supply the target sequence once to model 30, and then sample multiple points around the resulting output point in the latent space of the protein encoder output. The sampled points can then be used for molecule generation in molecular decoder 33. While generated compound data might possibly suggest existing drug compounds which would be active for a target protein, model 30 can exploit the full size of the chemical space for de novo design of novel drug compounds for target proteins.

Figure 11:
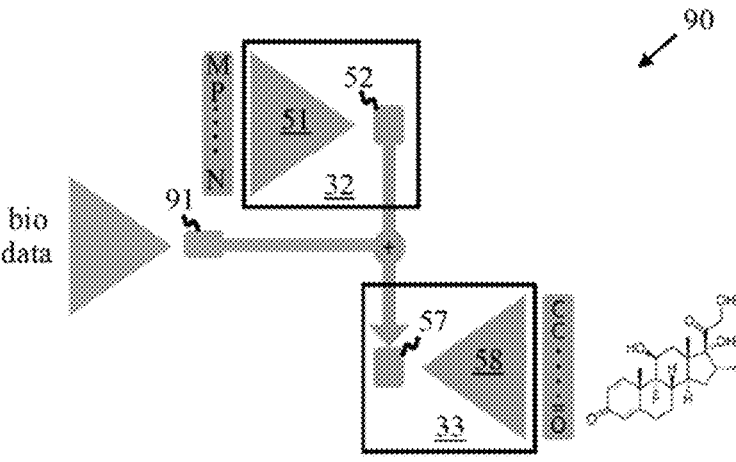
FIGS. 11 and 12 are schematic representations of modified neural network models in system embodiments.

Methods embodying the invention can also be adapted to tune the molecular design process for particular diseases, patients or drug types. The decoupled pretraining of model components 32, 33 provides smooth latent spaces for proteins and molecules respectively. The protein space can be readily fused with another latent space for further conditioning the molecular generation process. This is illustrated in FIG. 11 for a model 90 in which protein latent space 52 of protein encoder 32 is fused with an embedding space 91 for biomolecular (bio) data characterizing tissue cells. Such biomolecular data may comprise gene expression data, omics profiles of cells, or other biomolecular measurements representing a cell-samples of a particular disease, category of diseases and/or tissue type. When applying model 90 for inference, controller 41 generates a conditioning vector by embedding conditioning data, here biomolecular data, into embedding space 91, and this is then combined (here simply by addition 92) with the output vector of protein encoder 32 before sampling a point in latent space 57 of the molecular decoder 33. The input vector of the molecular decoder is thus further dependent on the conditioning vector, whereby the resulting compound data is conditioned on both the protein sequence and the conditioning bio-data. The conditioning vector may be generated from biomolecular data for particular disease cells to be targeted by the generated compounds, e.g. omics profiles of cancer cells or gene expression data of a particular patient. The drug design process can thus be tailored to a particular disease and/or patient. For a patient suspected to suffer from a certain type of cancer, for example, tumor biopsy is generally performed. Biomolecular measurements can then be made on the disease cells to obtain the biomolecular data for input to model 90. The resulting patient-specific drug compound data generated by model 90 can be used for personalized treatment planning for the patient. For example, the output compounds may be used to match existing drug compounds to the patient for selecting the most appropriate treatment. New disease-specific drug compounds can also be obtained by generating the conditioning vector from bio-data obtained from measurements on multiple cell samples for a particular disease, e.g. by averaging them.

Figure 12:
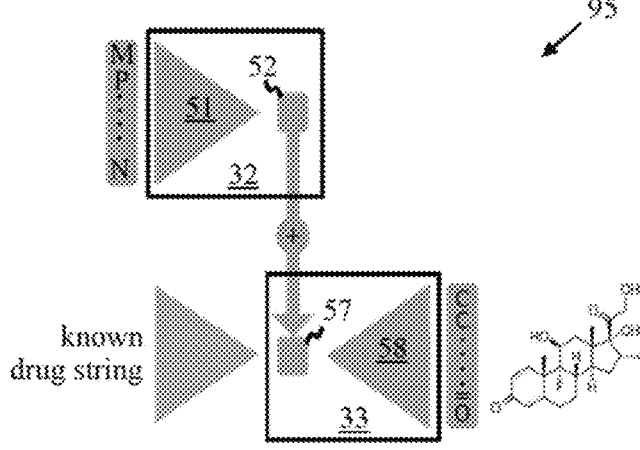

FIG. 12 illustrates another adaptation. In model 95 of this embodiment, a conditioning vector is generated by embedding compound data defining a known drug compound into the latent space 57 of molecular decoder 33. The output vector of protein encoder 32 is then combined (here added) to the conditioning vector to obtain the input vector for molecular decoder 33. This allows the drug design process to be conditioned on a known drug compound, e.g., with the aim of making small modifications to an existing drug, since moving small distances through smooth latent space 57 moves through points representing similar molecules.

Figure 13:
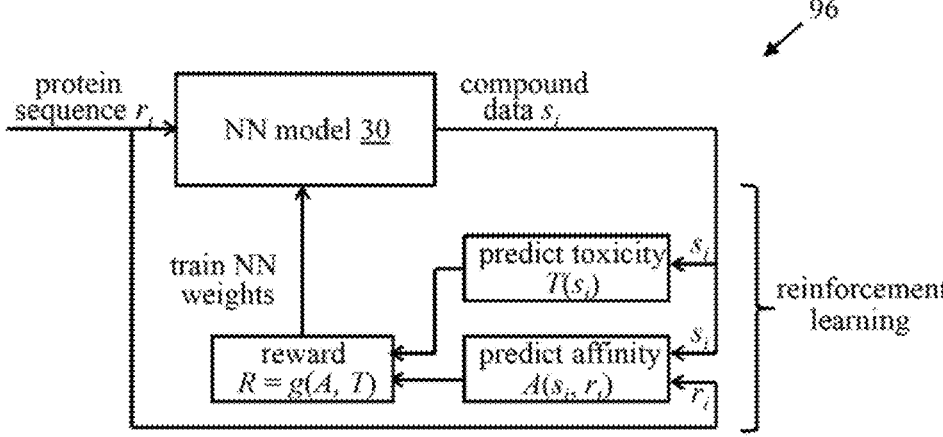
FIG. 13 illustrates a modification to the reinforcement learning architecture of FIG. 3.

Combinations of the above embodiments can also be envisaged, exploiting more than one conditioning vector in the conditional generative model. Further preferred embodiments allow the reinforcement learning architecture to train models to optimize additional properties. This is illustrated in FIG. 13 for an exemplary modification to the RL architecture of FIG. 3. In this RL architecture 96, the reward value R is a function g of both the affinity value $A(s_i, r_i)$ and a toxicity value T predictive of toxicity of the compound represented by string $s_i$. Such toxicity values may be generated by an additional critic NN which is pretrained to generate toxicity values for compound strings. Such a model may be implemented, for instance, by an MCA (multiple Correspondence Analysis) NN which is trained by supervised learning on a training dataset correlation drug compounds with toxicity, e.g. the Tox21 database. In this way, NN model 30 can be trained for conditional generation of compounds with both high protein affinity and low toxicity. RL architecture 100 can be adapted such that the reward value R is dependent one or more additional property values. Further examples include selectivity, water-solubility, drug-likeness and/or ease of synthesis. This technique may also be used to obtain drug compounds which have complementary or synergistic effects with a known drug compound. A critic network can be pretrained to generate a property value indicative of complementary/synergistic effect between two compounds defined by compound data input to the critic. When training model 30 in a modified RL architecture, similar to FIG. 13, using such a critic, the critic then receives both the compound data $s_i$ from model 30 and also compound data defining the known drug compound of interest. The property value output by this critic is then used, along with the affinity value A, in calculating the reward value R.

It will be appreciated that numerous other changes and modifications can be made to the exemplary embodiments described. For example, other mapping functions may be employed between protein encoder 32 and molecular decoder 33, and this mapping may be implemented by an additional neural network in some embodiments. Various other network architectures can also be envisaged, and networks may include additional processing stages, such as recurrent or convolutional neural network layers, where desired.

In general, where features are described herein with reference to a method embodying the invention, corresponding features may be provided in a system/computer program product embodying the invention, and vice versa.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for identifying drug compounds for targeting proteins in tissue cells, the method comprising:
providing a neural network model which comprises an attention-based protein encoder, pretrained in an autoencoder architecture to encode an input protein sequence into an output vector in a latent space representing proteins, and a molecular decoder which is pretrained in an autoencoder architecture to generate compound data, defining a compound molecule, from an input vector in a latent space representing molecules, wherein the protein encoder and molecular decoder are coupled such that the input vector of the molecular decoder is dependent on the output vector of the protein encoder for an input protein sequence;
training the model in a reinforcement learning architecture in which reward values dependent on affinity of compound molecules, defined by compound data generated by the molecular decoder for respective protein sequences encoded by the protein encoder, to proteins corresponding to those sequences are used to progressively train the model to optimize the reward value for compound data generated thereby;
after training the model, supplying a protein sequence for a target protein to the model to generate compound data corresponding to a set of drug compounds for targeting that protein;
matching one or more existing drug compounds to a given patient using the set of drug compounds;
selecting a treatment for the given patient based on the matching; and
facilitating the treatment of the given patient using the selected treatment.

2. The method according to claim 1 including generating a conditioning vector by embedding conditioning data, for conditioning generation of the compound data for a protein sequence, in an embedding space for that data, wherein the model is adapted such that the input vector of the molecular decoder is further dependent on said conditioning vector.

3. The method according to claim 2 including generating said conditioning vector by embedding biomolecular data for disease cells into an embedding space for biomolecular data.

4. The method according to claim 3 including making biomolecular measurements on disease cell samples to obtain said biomolecular data.

5. The method according to claim 2 including generating said conditioning vector by embedding compound data defining a known drug compound into said latent space representing molecules.

6. The method according to in claim 1 wherein:
said reinforcement learning architecture includes a critic neural network which is pretrained to generate, from an input protein sequence and input compound data defining a compound molecule, an affinity value indicating affinity of that compound molecule to the protein corresponding to that protein sequence; and
when training the model in said reinforcement learning architecture, a protein sequence encoded by the protein encoder and the compound data generated for that sequence by the molecular decoder are input to the critic neural network to obtain an affinity value for that compound data, said reward value for the compound data being dependent on the affinity value so obtained.

7. The method according to claim 1 wherein said reward value for the compound data is dependent on at least one further property value determined for the compound molecule defined by that compound data.

8. The method according to claim 6 wherein said at least one further property value is selected from values respectively indicative of toxicity, selectivity, water-solubility, drug-likeness, ease of synthesis, synergistic effect with a known drug compound, and complementary effect with a known drug compound.

9. The method according to claim 1 wherein the protein encoder comprises an embedding layer for encoding characters of an input protein sequence into respective character vectors in a character-embedding space, and an attention encoder for attention-based encoding of said character vectors into the output vector for the protein sequence.

10. The method according to claim 9 wherein the protein encoder comprises a transformer architecture.

11. The method according to claim 1 including pretraining the protein encoder and the molecular decoder in the respective autoencoder architectures.

12. The method according to claim 1 wherein said compound data comprises a string representation of a molecule.

13. A system for identifying drug compounds for targeting proteins in tissue cells, the system comprising:

a neural network model which comprises an attention-based protein encoder, pretrained in an autoencoder architecture to encode an input protein sequence into an output vector in a latent space representing proteins, and a molecular decoder which is pretrained in an autoencoder architecture to generate compound data, defining a compound molecule, from an input vector in a latent space representing molecules, wherein the protein encoder and molecular decoder are coupled such that the input vector of the molecular decoder is dependent on the output vector of the protein encoder for an input protein sequence; and control logic adapted to train the model in a reinforcement learning architecture in which reward values dependent on affinity of compound molecules, defined by compound data generated by the molecular decoder for respective protein sequences encoded by the protein encoder, to proteins corresponding to those sequences are used to progressively train the model to optimize the reward value for compound data generated thereby;

wherein the control logic is further adapted, in response to receipt of a protein sequence for a target protein after training the model, to supply the protein sequence to the model to generate compound data corresponding to a set of drug compounds for targeting that protein, to match one or more existing drug compounds to a given patient using the set of drug compounds, to select a treatment for the given patient based on the matching and to facilitate the treatment of the given patient using the selected treatment.

14. The system according to claim 13 wherein the model is adapted such that the input vector of the molecular decoder is further dependent on a conditioning vector which encodes conditioning data, for conditioning generation of the compound data for a protein sequence, in an embedding space for that data.

15. The system according to claim 14 wherein said conditioning data comprises biomolecular data for disease cells.

16. The system according to claim 14 wherein said conditioning data comprises compound data defining a known drug compound.

17. The system according to claim 13 wherein:

said reinforcement learning architecture includes a critic neural network which is pretrained to generate, from an input protein sequence and input compound data defining a compound molecule, an affinity value indicating affinity of that compound molecule to the protein corresponding to that protein sequence; and the control logic is adapted, when training the model in said reinforcement learning architecture, to input to the critic neural network a protein sequence encoded by the protein encoder and the compound data generated for that sequence by the molecular decoder to obtain an affinity value for that compound data, said reward value for the compound data being dependent on the affinity value so obtained.

18. The system according to claim 13 wherein said reward value for the compound data is dependent on at least one further property value selected from values respectively indicative of toxicity, selectivity, water-solubility, drug-likeness, ease of synthesis, synergistic effect with a known drug compound, and complementary effect with a known drug compound.

19. The system according to claim 13 wherein the protein encoder comprises an embedding layer for encoding characters of an input protein sequence into respective character vectors in a character-embedding space, and an attention encoder for attention-based encoding of said character vectors into the output vector for the protein sequence.

20. A computer program product for identifying drug compounds for targeting proteins in tissue cells, said computer program product comprising a non-transitory computer readable storage medium having program instructions embodied therein, the program instructions being executable by a computing system to cause the computing system to:

implement a neural network model which comprises an attention-based protein encoder, pretrained in an autoencoder architecture to encode an input protein sequence into an output vector in a latent space representing proteins, and a molecular decoder which is pretrained in an autoencoder architecture to generate compound data, defining a compound molecule, from an input vector in a latent space representing molecules, wherein the protein encoder and molecular decoder are coupled such that the input vector of the molecular decoder is dependent on the output vector of the protein encoder for an input protein sequence;

train the model in a reinforcement learning architecture in which reward values dependent on affinity of compound molecules, defined by compound data generated by the molecular decoder for respective protein sequences encoded by the protein encoder, to proteins corresponding to those sequences are used to progressively train the model to optimize the reward value for compound data generated thereby;

after training the model, supply a protein sequence for a target protein to the model to generate compound data corresponding to a set of drug compounds for targeting that protein;

match one or more existing drug compounds to a given patient using the set of drug compounds;

select a treatment for the given patient based on the matching; and facilitate treatment of the given patient using the selected treatment.

21. The method of claim 1, further comprising treating the given patient using the treatment selected based on the matching of the one or more existing drug compounds to the given patient.

* * * * *